(12) United States Patent
Leung et al.

(10) Patent No.: US 10,208,028 B1
(45) Date of Patent: Feb. 19, 2019

(54) METHODS OF TREATING CANCER

(71) Applicant: Macau University of Science and Technology, Macau (CN)

(72) Inventors: Lai Han Elaine Leung, Macau (CN); Xiao Jun Yao, Macau (CN); Liang Liu, Macau (CN); Jia Hui Xu, Macau (CN); Ying Li, Macau (CN); Qian Qian Wang, Macau (CN)

(73) Assignee: Macau University of Science and Technology, Macau (CN)

( * ) Notice: Subject to any disclaimer, the term of this patent is extended or adjusted under 35 U.S.C. 154(b) by 0 days.

(21) Appl. No.: 15/839,873

(22) Filed: Dec. 13, 2017

(51) Int. Cl.
| | | |
|---|---|---|
| *A61K 31/42* | (2006.01) | |
| *C07D 413/12* | (2006.01) | |
| *A61K 31/423* | (2006.01) | |
| *A61P 35/00* | (2006.01) | |
| *A61K 45/06* | (2006.01) | |
| *G01N 33/574* | (2006.01) | |

(52) U.S. Cl.
CPC .......... *C07D 413/12* (2013.01); *A61K 31/423* (2013.01); *A61K 45/06* (2013.01); *A61P 35/00* (2018.01); *G01N 2033/57453* (2013.01)

(58) Field of Classification Search
CPC .................................................. A61K 31/423
USPC ........................................................ 514/379
See application file for complete search history.

(56) References Cited

PUBLICATIONS

ACS RN902156-98-3. (Year: 2006).*
"What is Cancers," National Cancer Institute https://www.cancer.gov/about-cancer/understanding/what-is-cancer. (Year: 2018).*
Mayes, K., et al. (2014). ATP-Dependent Chromatin Remodeling Complexes as Novel Targets for Cancer Therapy. Adv Cancer Res, 121, 1-43.
Delmore, J. E., et al. (2011). BET Bromodomain Inhibition as a Therapeutic Strategy to Target c-Myc. Cell, 146, 904-917.
Kagoya, Y., et al. (2016). BET bromodomain inhibition enhances T cell persistence and function in adoptive immunotherapy models. The Journal of Clinical Investigation, 3479-3494.
Richart, L., et al. (2016). BPTF is required for c-MYC transcriptional activity and in vivo tumorigenesis. Nature communications, 7, 1-15.

(Continued)

*Primary Examiner* — Shengjun Wang
(74) *Attorney, Agent, or Firm* — Eagle IP Limited; Jacqueline C. Lui

(57) ABSTRACT

One embodiment is a method of treating cancer. The method includes administering a therapeutically effective amount of a compound to a patient. The compound is represented by Formula I:

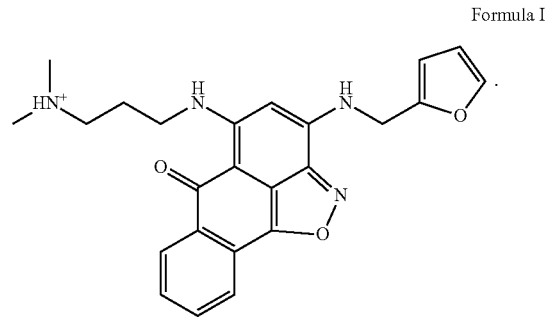

9 Claims, 10 Drawing Sheets
(4 of 10 Drawing Sheet(s) Filed in Color)

(56) References Cited

PUBLICATIONS

Dai, M., et al. (2015). BPTF promotes tumor growth and predicts poor prognosis in lung adenocarcinomas. Oncotarget, 6(32), 33878-33892.

Dar, A. A., et al. (2016). BPTF transduces MITF-driven prosurvival signals in melanoma cells. Proceedings of the National Academy of Sciences, 113(22), 6254-6258.

Wadhwa, E., et al. (2016). Bromodomain Inhibitor Review: Bromodomain and Extra-terminal Family Protein Inhibitors as a Potential New Therapy in Central Nervous System Tumors. Cureus, 8(5).

Landry, J. W., et al. (2010). Chromatin remodeling complex NURF regulates thymocyte maturation. Genes & development, 25, 275-286.

Urick, A. K., et al. (2015). Dual Screening of BPTF and Brd4 Using Protein-Observed Fluorine NMR Uncovers New Bromodomain Probe Molecules. ACS chemical biology 10(10), 2246-2256.

Chen, Q. W., et al. (2014). Epigenetic regulation and cancer. Oncology reports, 31, 523-532.

Sharma, S., et al. (2010). Epigenetics in cancer. Carcinogenesis, 31(1), 27-36.

Alamgeer, M., et al. (2013). Novel therapeutic targets in non-small cell lung cancer. Current Opinion in Pharmacology, 13, 394-401.

Ruthenburg, A. J., et al. (2011). Recognition of a Mononucleosomal Histone Modification Pattern by BPTF via Multivalent Interactions. Cell, 145, 692-706.

Xiao, S., et al. (2015). The prognostic significance of bromodomain PHD-finger transcription factor in colorectal carcinoma and association with vimentin and E-cadherin. Journal of cancer research and clinical oncology, 141(8), 1465-1474.

Dar, A. A., et al. (2015). The Role of BPTF in Melanoma Progression and in Response to BRAF-Targeted Therapy. Journal of the National Cancer Institute, 107(5).

Spira, A., et al. (2016). Update in Lung Cancer 2015. American Journal of Respiratory and Critical Care Medicine, 194(6), 661-671.

\* cited by examiner

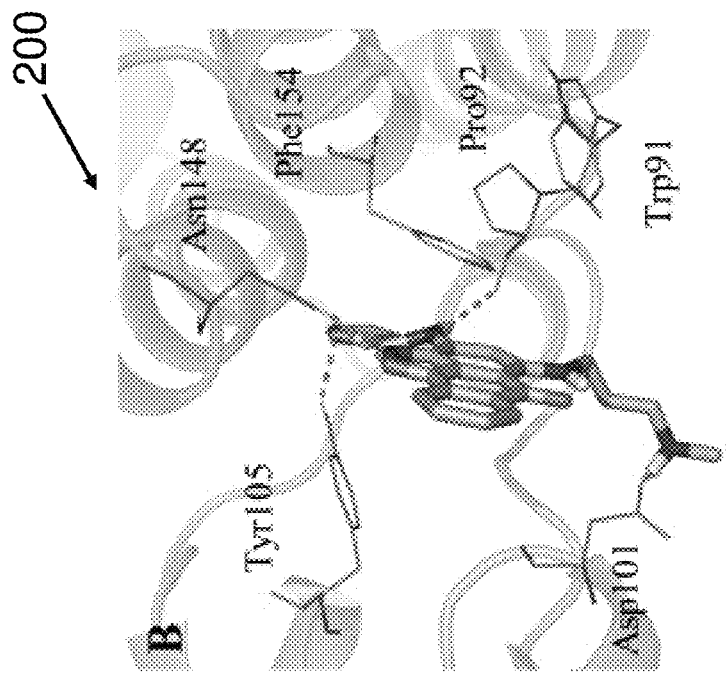
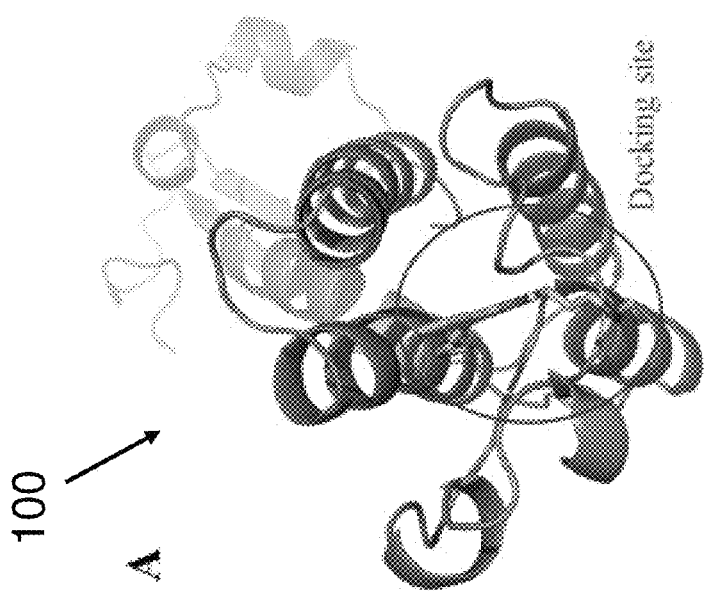
Fig. 1B
Fig. 1A

D

| Cell line | IC$_{50}$ (μM) |
|---|---|
| A549 | 11.2 ± 0.74 μM |
| H358 | 6.72 ± 1.35 μM |

METHODS OF TREATING CANCER

FIELD OF THE INVENTION

The present invention relates to a method of treating cancer. In particular, the present invention relates to inhibitors that target chromatin remodeling factors.

BACKGROUND

Cancer is the most common cause of death all over the world. In addition to genetic changes of driver genes in cancer, epigenetic alterations such as changes in DNA methylation, histone modifications, and chromatin organization (e.g., nucleosome remodeling) impact gene expression and cellular gene function, and play an important role in the onset and progression of cancer. Bromodomains are proteins with acetyl-lysine binding modules and have a key role in transcriptional activation. Clinical trials are underway evaluating inhibition of several members of the bromodomains and extra terminal (BET) family proteins (i.e., Brd2, 3, 4) in cancer.

In view of the demand for treating cancer in a patient, more methods and compositions that effectively treat cancer are desired.

SUMMARY

One example embodiment is a method of treating cancer in a patient. The method includes administering to the patient a therapeutically effective amount of a compound of Formula I as follows:

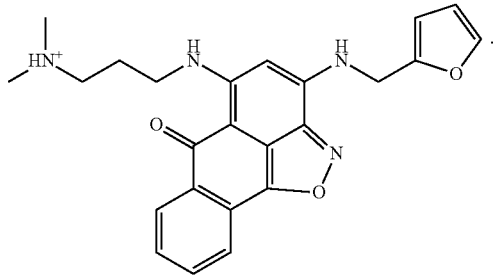

Formula I

Other example embodiments are discussed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows a docking site of compound C620-0696 on the bromodomain of Bromodomain Plant Homeodomain (PHD) Finger Transcription Factor (BPTF) in accordance with an example embodiment.

FIG. 1B shows a binding mode between compound C620-0696 and the bromodomain of BPTF in accordance with an example embodiment.

DETAILED DESCRIPTION

Figures 2A, 2B:
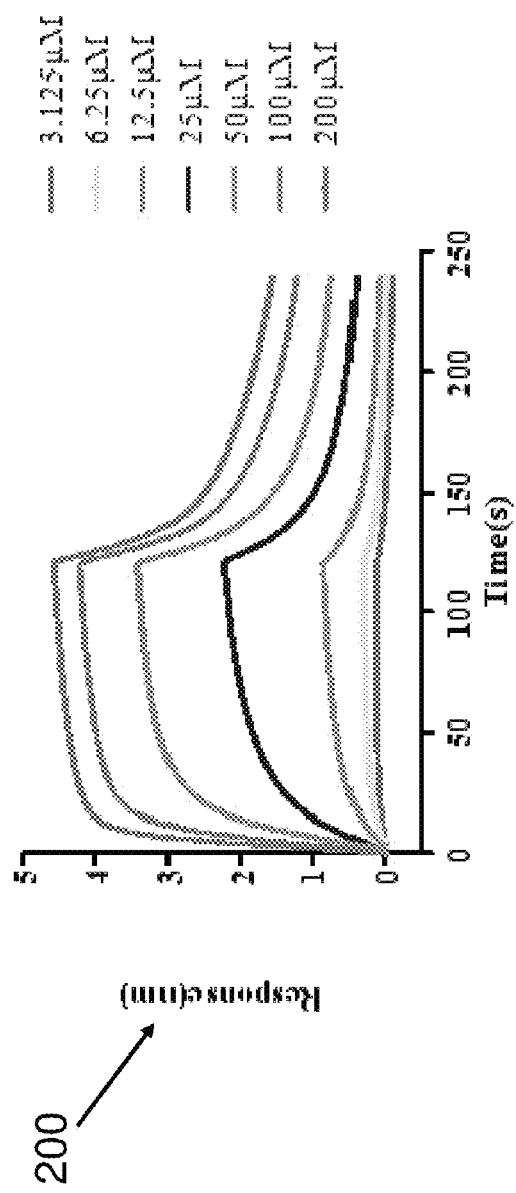
FIG. 2A shows determination of the binding affinity of the bromodomain of BPTF with compound C620-0696 by Bio-layer interferometry assay in accordance with an example embodiment.
FIG. 2B shows the binding affinity (KD) of the bromodomain for compound C620-0696 was determined by the rate constants of $Kon=4.78\times 102$ $M^{-1}$ $S^{-1}$ and $Koff=1.70\times 10^{-2}$ $S^{-1}$ in accordance with an example embodiment.

Example embodiments relate to methods of treating cancer. The methods include administering a therapeutically effective amount of a compound to a patient. The compound is represented by Formula I:

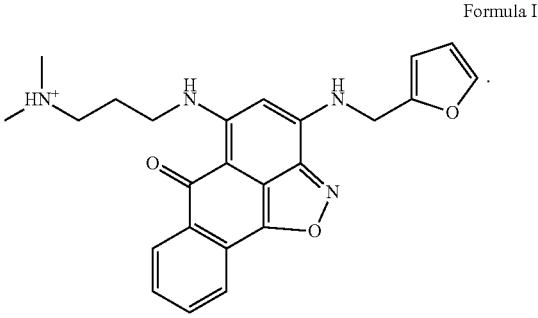 [SMILES: C[NH+](C)CCCNc1cc(NCc2ccco2)c2noc3c2c1C(=O)c1ccccc1-3]

Formula I

In one example embodiment, the cancer is associated with overexpression or high expression of Bromodomain Plant Homeodomain (PHD) Finger Transcription Factor (BPTF).

BPTF is the largest unit of nucleosome remodeling factor (NURF), which mainly regulates genes transcription and mediates histone modification essential for the development of key tissues in chromatin remodeling. High BPTF expression is significantly associated with tumor progression and promotes tumor cell proliferation and metastasis in cancer. In an example embodiment, the cancer includes but not limited to colorectal cancer, melanoma, breast cancer, lung adenocarcinoma, and brain cancer. BPTF is also related with poor prognosis in cancer including lung adenocarcinomas. BPTF displays an essential role in tumor cell growth and survival by targeting multiple signaling pathways in cancer including non-small cell lung cancer.

The bromodomain of BPTF specifically recognizes histone H4K16 acetylation, which performs its essential regulation of chromatin structure in development. Overexpression of BPTF that interacts with histone H4K16 acetylation promotes tumor cell growth, proliferation and metastasis. An example embodiment provides compound C620-0696 (i.e., the compound of Formula I) which inhibits the interaction between the bromodomain of BPTF and histone H4K16 acetylation in cancer, such that the cancer can be treated.

An example embodiment provides a method to target a bromodomain factor meditated tumorigenesis in cancers with small molecules. An example embodiment also provides a BPTF inhibitor, compound C620-0696, that targets the bromodomain of BPTF with −9.187 kcal/mol docking score determined by the molecular docking analysis. Compound C620-0696 exhibits a high binding affinity to the bromodomain of BPTH with $K_D$ of 35.5 μM in vitro by using biolayer interferometry (BLI). Compound C620-0696 is cytotoxic in BPTF high expressing cancer cells. Compound C620-0696 inhibits the migration and colony formulation of cancer cells. Compound C620-0696 induces cell apoptosis by increasing the levels of cleaved Poly (ADP-ribose) polymerase (PARP) protein and blocked cell cycle by inhibiting the expression of cyclin D1 in cancer cells. Compound C620-0696 suppresses the expression of an oncogenic transcriptional regulator c-MYC, which can regulate cell growth and drive tumorigenesis.

An example embodiment provides a method of treating cancer in a patient by administering compound C620-0696 to the patient. In one example embodiment, tumor cells of the cancer express a higher level of BPTF than normal cells express. In one example embodiment, tumor cells of the cancer express a higher level of BPFT than healthy cells express. In one example embodiment, the cancer is selected from a group consisting of colorectal cancer, melanoma, breast cancer, lung adenocarcinoma, and brain cancer. In one example embodiment, the cancer is non-small cell lung cancer.

In one example embodiment, compound C620-0696 is administered in combination with one or more additional BPTF inhibitors to the patient.

In one example embodiment, a patient is diagnosed as the patient with the cancer by determining an expression level of BPTF. If the expression level of BPTF is higher than that of normal or healthy cells or tissues, the patient is diagnosed as the cancer that can be treated by compound C620-0696.

An example embodiment provides a method of treating a disease associated with overexpression of BPTF. The disease associated with overexpression of BPTF relates to the interaction between the overexpressed BPRF and histone H4K16 acetylation. Compound C620-0696 inhibits the interaction between BPTF and histone H4K16 acetylation and thereby ameliorate the progress of the disease associated with overexpression of BPTF.

In one example embodiment, the disease associated with overexpression of BPTF includes but not limited to cancer including colorectal cancer, melanoma, breast cancer, lung adenocarcinoma, and brain cancer.

An example embodiment provides a pharmaceutical composition that includes compound C620-0696.

In one example embodiment, the pharmaceutical composition is used to treat cancer. In one example embodiment, tumor cells of the cancer express a higher level of BPTF than normal cells do. In one example embodiment, the cancer is selected from a group consisting of colorectal cancer, melanoma, breast cancer, lung adenocarcinoma, and brain cancer. In one example embodiment, the cancer is non-small cell lung cancer. In one example embodiment, the pharmaceutical composition is used to treat a disease associated with overexpression of BPTF.

In one example embodiment, the pharmaceutical composition includes one or more additional BPTF inhibitors. In one example embodiment, the pharmaceutical composition includes a pharmaceutically acceptable excipient or carrier. The pharmaceutically acceptable excipient or carrier includes but not limited to fillers (diluents), binders, disintegrating agents, lubricants, and glidants.

In one example embodiment, the pharmaceutical compositions can be administered by various routes, e.g., oral, subcutaneous, transdermal, intramuscular, intravenous, or intraperitoneal. Routes of administering the pharmaceutical composition include systematic delivery or local delivery to an organ or tissue.

Example 1 Material and Methods

Cell Culture

A549 and H358 cell lines were stored in liquid nitrogen. A549 and H358 cells were cultured by RPMI 1640 medium after recovery. RPMI 1640 medium supplemented with 10% fetal bovine serum and 100 units/mL penicillin and 100 μg/mL streptomycin. A549 and H358 cells were grown at 37° C. incubator with 5% $CO_2$.

MTT Assay

All compounds were dissolved in dimethyl sulfoxide (DMSO) and stored at −40° C. HCC78 cells were plated in 96-well micro-plate and plated 3000 cells/well. Then the 96-well micro-plate was put back in the incubator and overnight for cell adhesion. After cell adhesion, the medium was removed and each well was added with 100 μl drug-containing medium. There were three different concentrations for each drug and three duplicate wells for each concentration. Then cell adhesion was cultured overnight for 72 hr. After 72 hr, each well was added with 10 μl of MTT solution and the 96-well plate was put back in the incubator for 4 hr. Then 100 μl of the SDS solution (10% SDS and 0.1 mM HCL) was added to each well and incubated at 37° C. for 4 hr. Finally the absorbance of the plate was measured by an absorbance reader (Tecan, Morrisvill, N.C., USA).

Colony Formation Assay

Cell survival was assessed by colony formation as previously described. A549 cells were seeded to six-well plate (500-1000/well). Then cells were exposed to various doses of compound C620-0696. After 7 days, colonies were fixed with 4% paraformaldehyde for 15 minutes and stained with crystal violet for 10-15 minutes. Finally, the staining solution was slowly washed off with water and the cells were air dried.

Wound Healing Assay

A549 cells were seeded onto 6 well plates. When the cell confluence reached about >90% and scratch wounds were made by scraping the cell layer across each plate using the tip of 200 μl pipette. Wounded cultures were incubated in medium for 48 hr, and then visualized by Olympus inverted microscopy to assess cell migration ability.

Western Blot Analysis

The cell culture dish was placed in the ice and washed the cells with PBS. Then the PBS was removed to ensure that the cells were lysed in cell lysis buffer containing protease and phosphatase inhibitors. Adherent cells were scraped off from the plate and transferred the lysate into a new tube. The tube was maintained at a constant agitation for 15 min in the ice. Then the tubes were centrifuged at 4° C. 12000 g for 5 min. The supernatant was transferred into a new tube and 4× loading buffer was added to the supernatant. Each sample was boiled at 100° C. for 5 min. Equal amounts of protein (50 µg) were loaded into the wells of a SDS-PAGE gel, along with 3 µl markers. The gel was placed in transfer buffer in sandwich and was transferred to a nitrocellulose filter membrane. After transferring for 3 hr in an ice bucket at a constant current of 300 mA, the membranes were blocked in 5% non-fat milk in TBST at room temperature for 1 hr. The membrane was incubated overnight with the primary antibody solution, against the target protein at 4° C. The blot was rinsed 3 times within 5 min with TBST. The secondary antibody solution was incubated for 1 hr at room temperature. All primary antibodies were diluted 1:1000, while their recommended secondary antibodies were diluted 1:10000. The LI-COR Odessy scanner (Befast, Me., USA) was used to detect the result of western blot.

Kinetic binding analysis by biolayer interferometry.

The Octet Red96 system (Forte Bio, Pall) was used to determine the binding between compound C620-0696 and BPTF. BPTF protein was loaded to saturation onto anti-His capture sensors (ForteBio), then was placed for 2 min in wells containing C620-0696 (concentrations: 3.125, 6.25, 12.5, 25, 50, 100, 200 µM). The baseline and dissociation steps were carried out in the kinetics buffer as per the instrument manufacturer's recommendations. Kinetic binding data in all cases were adequately described accurately by a 1:1 binding model.

Molecular Docking

The 3D structure of BRD4-benzoisoxazoloazepine 3 complex (PDBID: 5HM0) was obtained from PDB database. After the preparation of BPTF with Prep Wiz in Maestro (Schrodinger 2015), a grid file was generated centered on benzoisoxazoloazepine 3 in this complex. Compound C620-0696 was then preprocessed by LigPrep under OPLS-2005 force field. Finally, Glide with the standard precision (SP) scoring mode was used to dock compound C620-0696 into BPTF binding pocket. The pose with the lowest docking score was chosen for further binding mode analysis.

Example 2 a Small-Molecule Compound C620-0696 Identified as an Inhibitor of the Bromodomain Ligand of BPTF FIG. 1A shows the interaction 100 between compound C620-0696 and BPTF. The docking site between compound C620-0696 and the bromodomain of BPTF is shown in the red circle of FIG. 1A.

Compound C620-0696 was identified as a small molecule that inhibits the interaction between the bromodomain of BPTF and H4K16ac. The molecular docking calculation was performed on analyzing the interaction of the bromodomain of BPTF with compound C620-0696 by Induced Fit Docking module in Schrodinger15 software. After computationally docking and testing, the small-molecule compound C620-0696 as the BPTF inhibitor has the docking score −9.187 kcal/mol.

FIG. 1B shows the binding mode 200 between compound C620-0696 and the bromodomain of BPTF. Green dashed lines represent hydrogen bonds.

The large aromatic plane of compound C620-0696 inserted into a hydrophobic pocket including Pro92, Asp101, Tyr105, Asn148 and Phe154. When interacting with the bromodomain of BPTF, compound C620-0696 formed five hydrogen bonds with residue Pro92, Asp101, Tyr105 and Asn148 as shown in FIG. 1B. In addition, compound C620-0696 also formed pai-pai stacking interaction with Phe154, further strengthening the binding between the bromodomain of BPTF and compound C620-0696.

Example 3A Kinetics of the Interaction Between Compound C620-0696 and the Bromodomain Ligand of BPTF FIG. 2A is a graph 200 showing the binding affinity of the bromodomain of BPTF with compound C620-0696 by Biolayer interferometry assay (BLI). BLI is a label-free technology for measuring biomolecular interactions. The bromodomain was immobilized on the streptavidin (SA) biosensors, and then mixed with different concentration of compound C620-0696 at 3.125, 6.25, 12.5, 25, 50, 100, 200 µM. Finally, the steady-state analysis was performed to obtain the binding affinity with KD value of 35.5 µM (FIG. 2B). These results indicated that compound C620-0696 exhibited a high binding affinity to the bromodomain of BPTF.

Figure 3A:
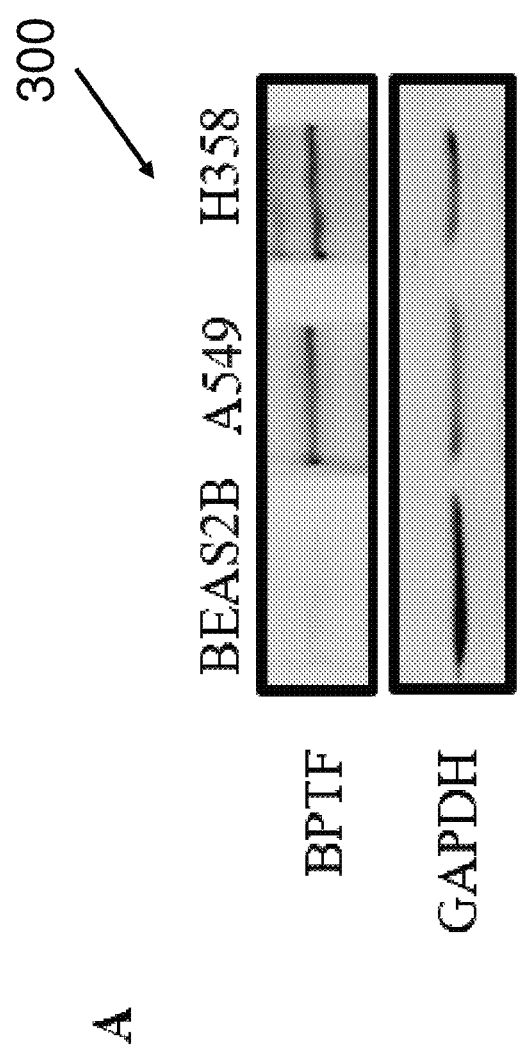
FIG. 3A shows the western blot analysis for the BPTF expression in the Human Bronchial Epithelial Cell (BEAS-2B), A549 and H358 cell lines in accordance with an example embodiment.

Example 3B Cytotoxicity of Compound C620-0696 in Non-Small Cell Lung Cancer (NSCLC) Cells with High BPTF Expression FIG. 3A shows the western blot analysis 300 for the BPTF expression in the Human Bronchial Epithelial Cell (BEAS-2B), A549 and H358 cells.

To investigate whether compound C620-0696 could inhibit BPTF function in vitro, BPTF high expressing NSCLC cell lines (A549 and H358) as the cell models were selected for this study, compared to BEAS-2B as shown in FIG. 3A. GAPDH was used as loading control. The result of FIG. 3A shows that the expressions of BPTF in A549 and H358 cells are higher than that in BEAS-2B.

Figure 3B:
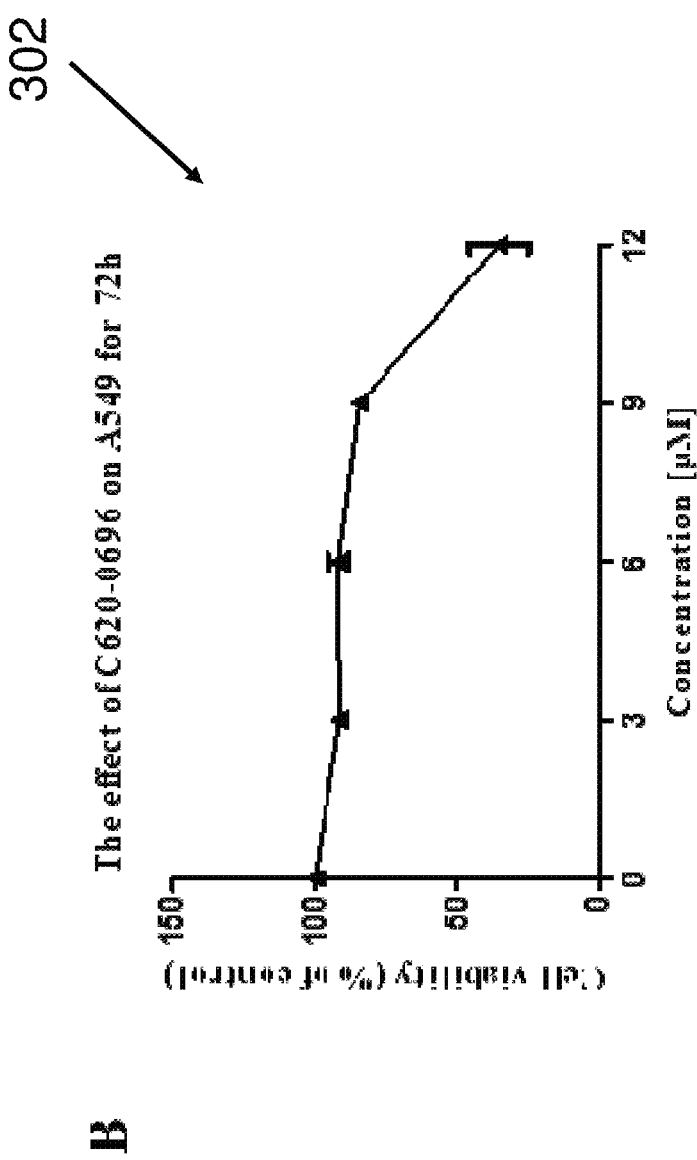
FIG. 3B shows cell viability measured in A549 cells treated with compound C620-0696 at 3, 6, 9 and 12 μM for 72 hr in accordance with an example embodiment.
Figure 3C:
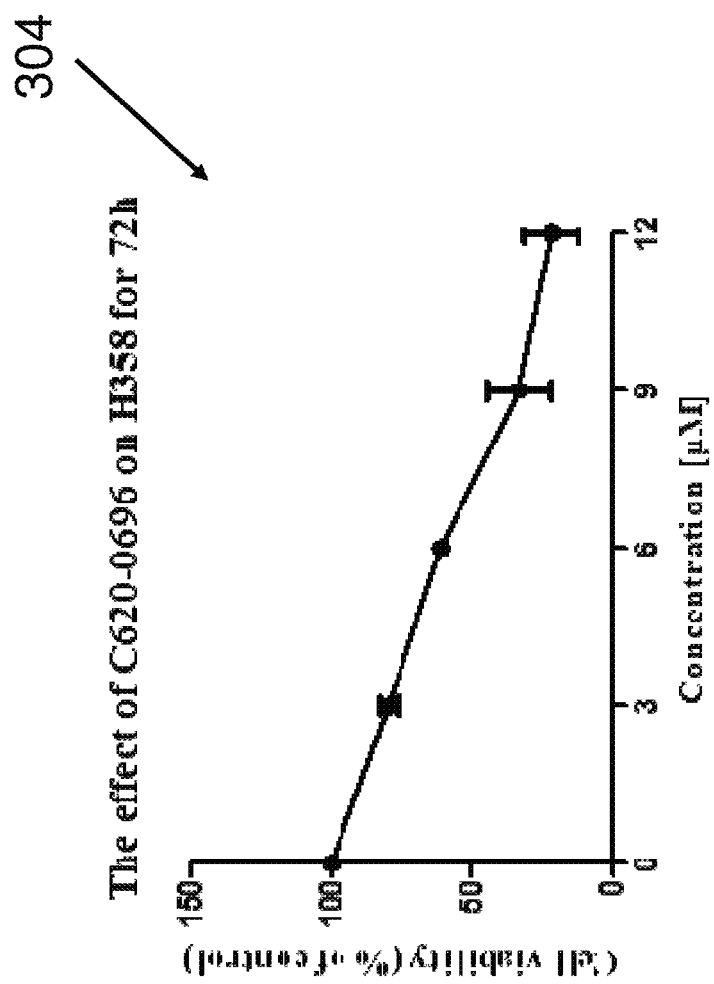
FIG. 3C shows cell viability measured in H358 cells treated with compound C620-0696 at 3, 6, 9 and 12 μM for 72 hr in accordance with an example embodiment.
Figure 3D:
FIG. 3D shows the $IC_{50}$ (the half maximal inhibitory concentration) value calculated in compound C620-0696 treated A549 and H358 cells in accordance with an example embodiment.

FIG. 3B is a graph 302 showing the effect of compound C620-0696 on the cell viability of A549 cells. A549 cells were treated by different concentrations of compound C620-0696, i.e. 3, 6, 9 and 12 µM for 72 hr. FIG. 3C is a graph 304 showing the effect of compound C620-0696 on the cell viability of H358 cells. H358 cells were treated by different concentrations of compound C620-0696, i.e. 3, 6, 9 and 12 µM for 72 hr. FIG. 3D is a table 306 showing the $IC_{50}$ value in A549 and H358 cells treated by compound C620-0696. Compound C620-0696 inhibited cell viability with $IC_{50}$ of 11.2 µM for A549 cells and 6.72 µM for H358 cells at 72 hr treatment, respectively. These results indicated that compound C620-0696 exhibited significantly cytotoxic effect on NSCLC with high BPTF expression.

Figure 4:
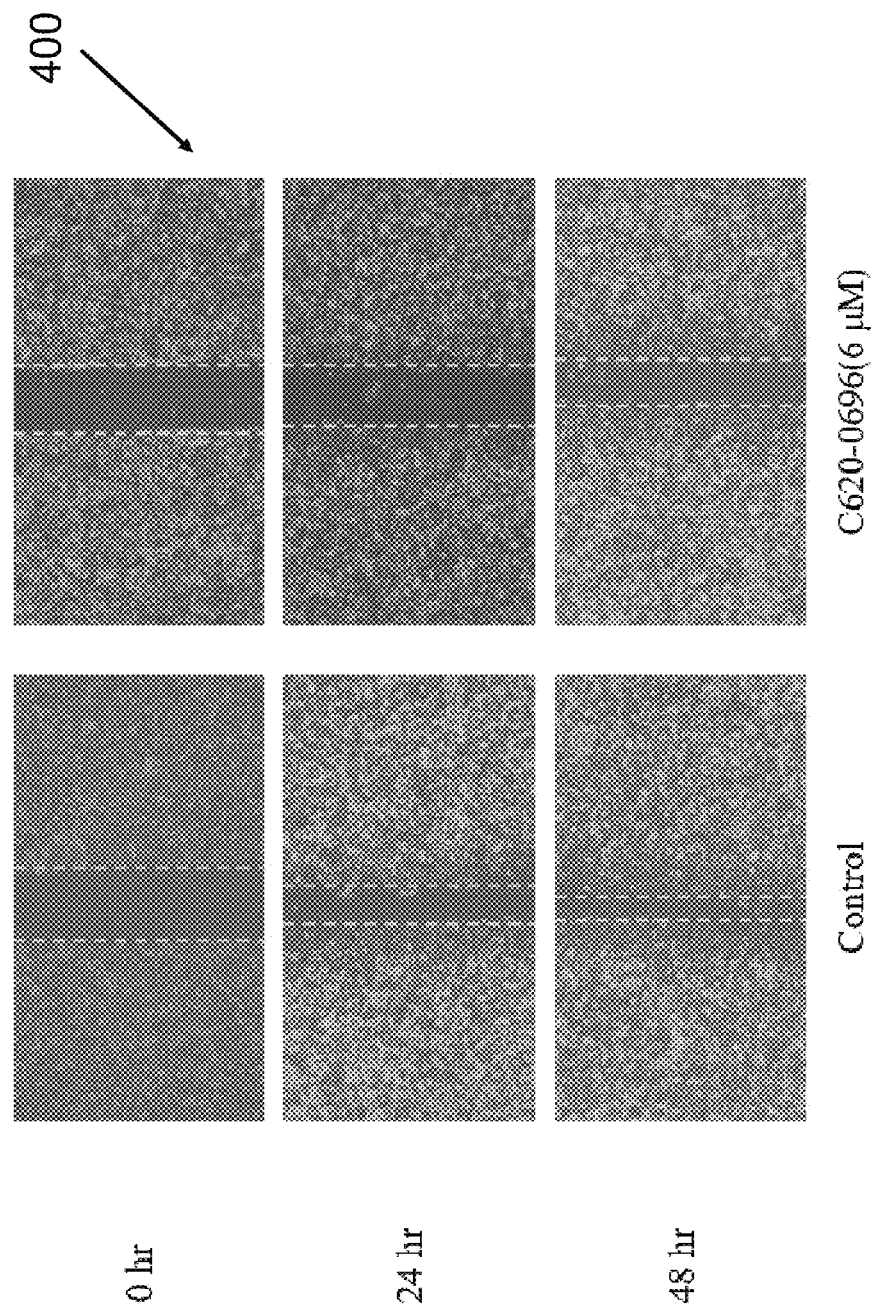
FIG. 4 shows would healing assay in response to compound C620-0696 in A549 cells in accordance with an example embodiment. Motility of compound C620-0696 treated cells or control cells was captured after 24 and 48 hours postinjury, respectively. Images of a representative wound (10×) were shown in a dashed yellow line.

Example 4 Effect of Compound C620-0696 on the Inhibition of the Migratory Capacity of A549 Cells FIG. 4 are drawings 400 showing the wound healing assay in A549 cells treated by compound C620-0696.

To evaluate the effect of C620-0696 on cell migration and cellular processes in NSCLC, the wound healing assay was employed to assess the directional cell motility in A549 cells. The results of FIG. 4 indicated that over time A549 cells migrated more slowly in compound C620-0696 treatment group compared with the control cells, supporting that inhibition of BPTF reduced the migratory capacity of NSCLC cells.

Figure 5:
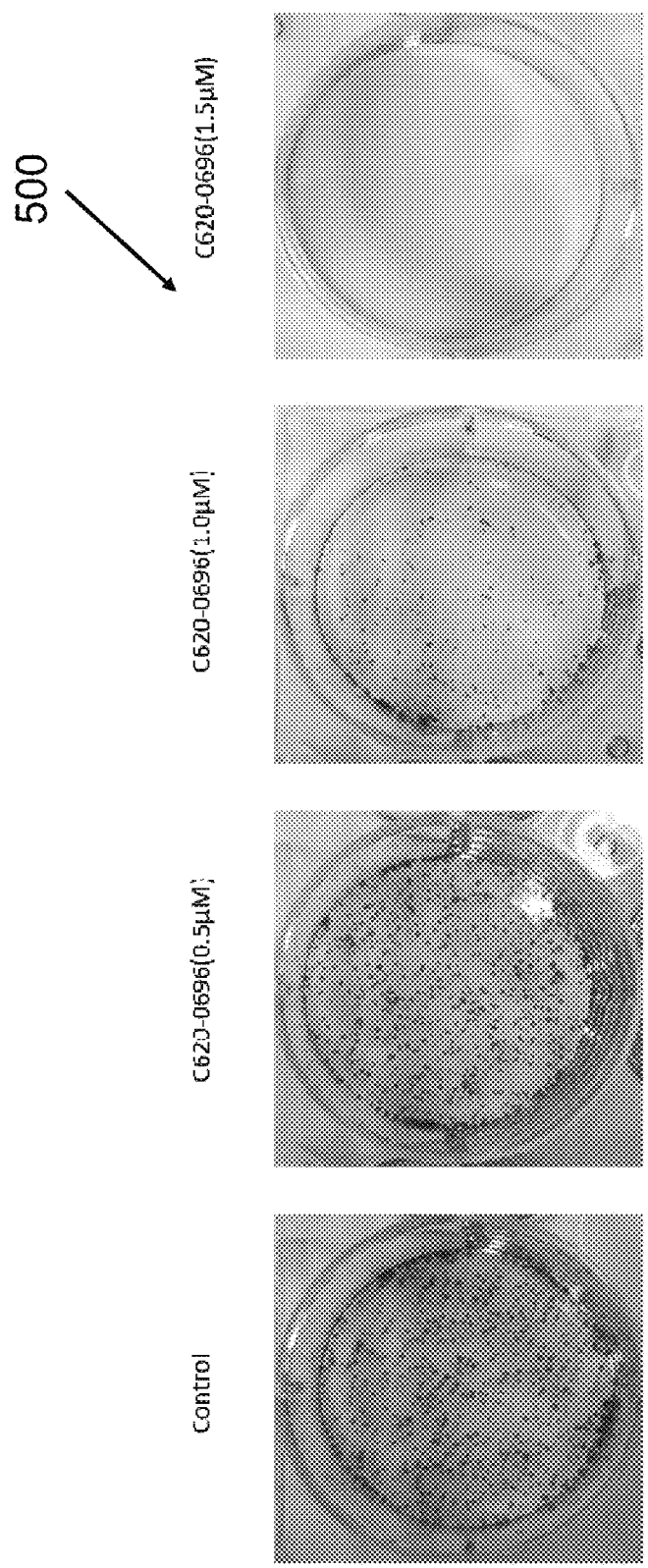
FIG. 5 shows colony formation assay of A549 cells with compound C620-0696 treatment at 0, 0.5, 1, 1.5 μM in accordance with an example embodiment.

Example 5 Effect of Compound C620-0696 on the Inhibition of Colony Formation of A549 Cells FIG. 5 shows colony formation assay 500 in A549 cells treated by compound C620-0696.

To determine the effect of the compound C620-0696 on A549 cell growth behavior, a colony formation assay was performed. A549 cells were treated by different concentrations of compound C620-0696, i.e. 0 (control group), 0.5, 1, 1.5 µM. As shown in FIG. 5, a significant loss of colony formation in A549 cells treated with compound C620-0696 in dose-dependent manner was observed, compared with control group. These results indicated that compound C620-0696 inhibited cell growth and proliferation.

Figure 6:
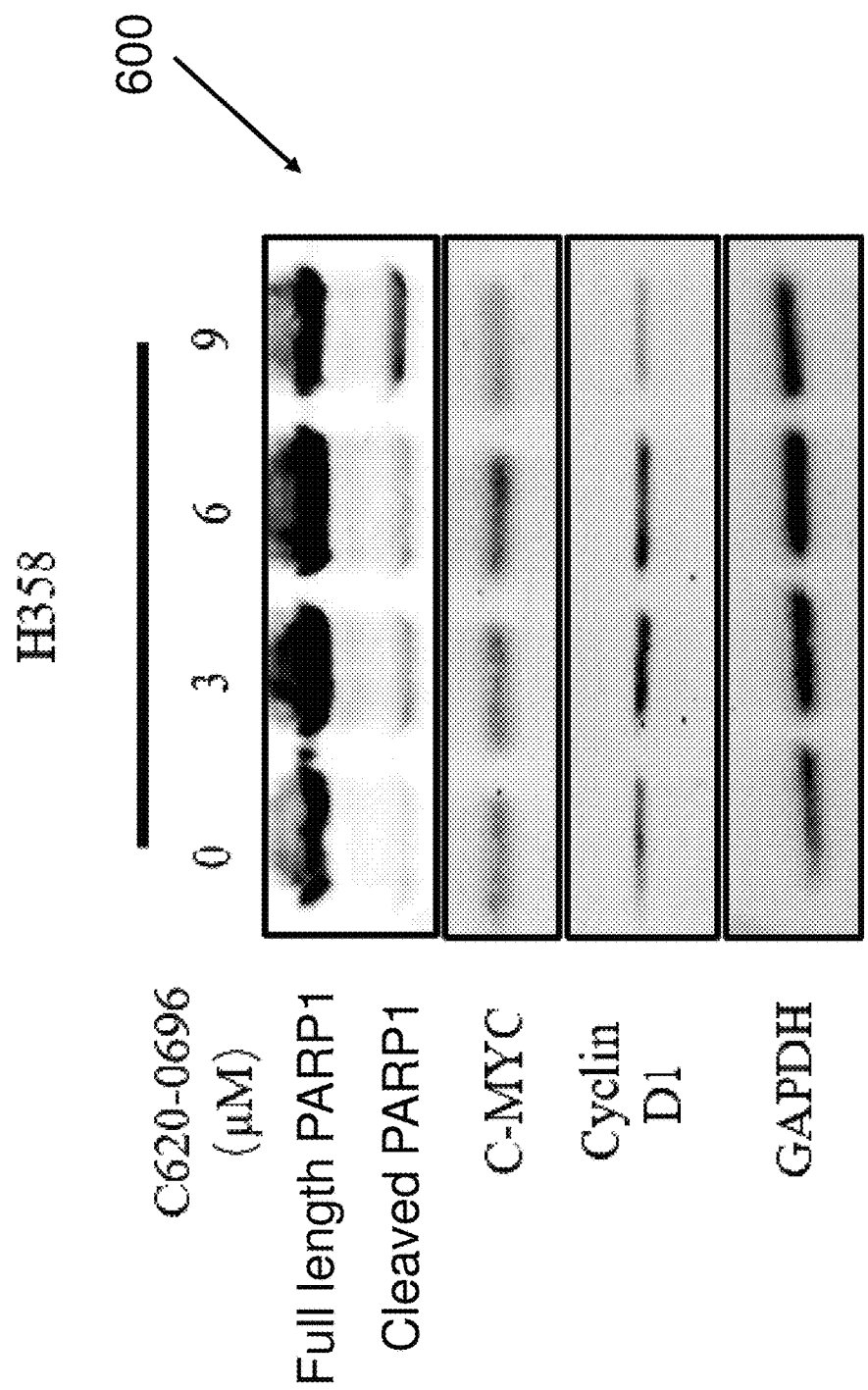
FIG. 6 shows western blot analysis for the expression levels of PARP1 (Poly [ADP-ribose] polymerase 1), c-MYC and Cyclin D1 while GAPDH was used as loading control in A549 cells treated with compound C620-0696 at 0, 3, 6, 9 μM for 24 hr in accordance with an example embodiment.

Example 6 Effect of Compound C620-0696 in Inducing Apoptosis in H358 Cells and Suppressing Cell Cycle FIG. 6 shows the western blot analysis 600 for the expression level of PARP1, c-MYC and Cyclin D1. GAPDH was used as loading control in H358 cells treated with compound C620-0696 at 0, 3, 6, 9 µM for 24 hr.

To determine whether the induction of apoptosis in NSCLC cells was contributed by compound C620-0696-mediated growth inhibition, cleaved PARP1 in compound C620-0696 treated H358 cells was detected. Compound C620-0696 significantly increased the levels of cleaved PARP1 at concentration of 9 µM as shown in FIG. 6. Compound C620-0696 induced apoptosis by increasing the levels of cleaved PARP1. In addition, compound C620-0696 reduced the expression of cyclin D1 related to cell cycle in H358 cells, and suppressed the expression of an oncogenic transcriptional regulator c-MYC (FIG. 6), which was a BPTF target gene in tumorigenesis. These data suggested that compound C620-0696 inhibited BPTF transcriptional regulation of its target oncogenic genes, thereby leading to cell apoptosis induction and cell cycle suppression in NSCLC.

FIGS. 1-6 shows that compound C620-0696 as an inhibitor could target the bromodomain of chromatin remodeling factor BPTF. Compound C620-0696 exhibited a high binding affinity to the bromodomain of BPTF. Moreover, MTT assay showed compound C620-0696 was cytotoxic in BPTF high expressing NSCLC cell lines H358 and A549. Compound C620-0696 also inhibited the migration and colony formation of A549 cells. In addition, compound C620-0696 induced apoptosis in H358 cells and suppressed the expression of c-MYC and Cyclin D1. These findings indicated an effective strategy to target a bromodomain factor meditated tumorigenesis in cancers with compound C620-0696. It also provides methods of treating diseases associated with high expression of BPTF by targeting the bromodomain of BPTF.

Figure 7:
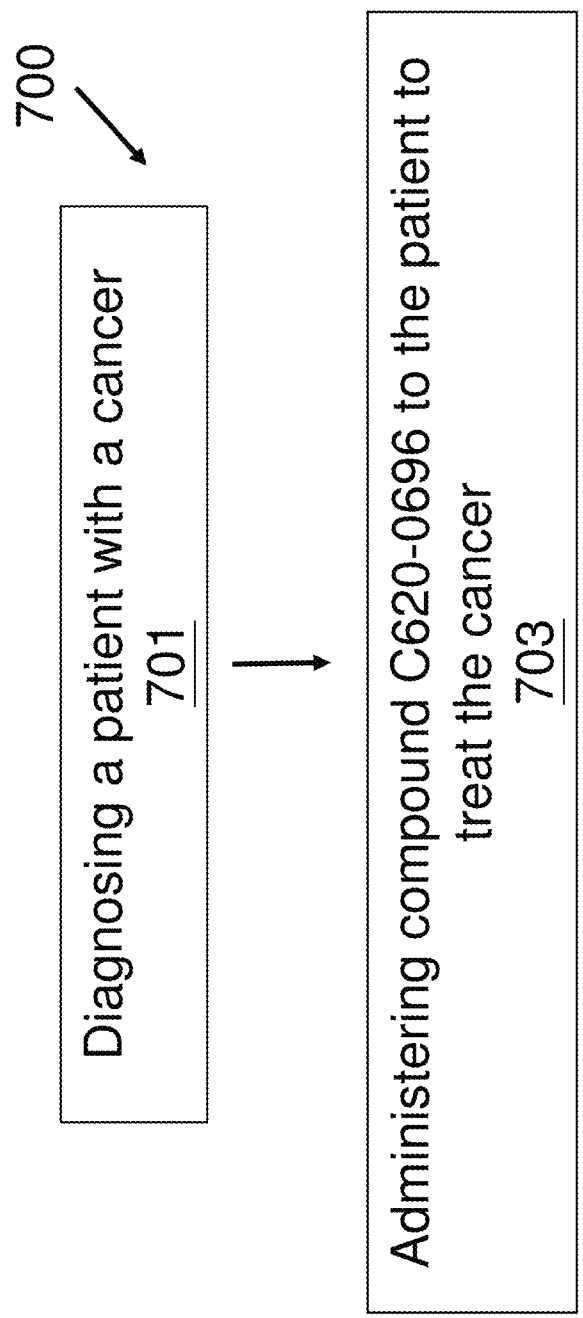
FIG. 7 shows a method of treating cancer in a patient in accordance with an example embodiment.

FIG. 7 shows a method 700 of treating cancer in a patient. Block 701 states diagnosing a patient with a cancer. In one example embodiment, a biological sample is obtained from a patient. Whether BPTF is overexpressed in the biological sample is detected by comparing a level of BPTF overexpression in the biological sample with a level of BPTF expression in a control group. If the level of the BPTF expression in the biological sample is higher than that in the control group, the patient is diagnosed as the patient with the cancer.

In one example embodiment, the biological sample is a tissue sample, a blood sample or a plasma sample from the patient. In one example embodiment, the biological sample is obtained by biopsies. In one example embodiment, the control group is a biological sample from a normal or healthy sample, cells or tissues. In one example embodiment, the control group is a biological sample from a normal or healthy person.

Block 703 states administering compound C620-0696 to the patient to treat the cancer.

In one example embodiment, the compound is administered directly or in the form of pharmaceutical compositions with suitable carriers or excipients. In one example embodiment, suitable routes of administration may, for example, include oral, rectal, transmucosal, nasal, or intestinal administration and parenteral delivery. The compound or the pharmaceutical composition that includes the compound can be administered locally. For example, the compound can be delivered via injection or in a targeted drug delivery system, such as a depot or sustained release formulation.

In one example embodiment, the cancer is the cancer associated with overexpression of BPTF. In one example embodiment, the cancer is the cancer whose tumor cells express a higher level of BPTF than normal cells express. In one example embodiment, the cancer is lung cancer. In one example embodiment, the cancer is non-small cell lung cancer.

As used herein, the term "administration" or "administering" refers to providing a compound of an example embodiment and/or prodrugs thereof to a person in need of treatment.

As used herein, the term "BPTF inhibitor" refers to a therapeutic agent that can reduce or inhibit overexpression of BPTF, or the activity of BPTF, or the interaction between BPTF and histone H4K16 acetylation.

As used herein, the term "disease associated with overexpression of BPTF" refers to a disease that is associated with or characterized by a higher expression of BPTF compared with that of normal or healthy sample including cells or tissues.

As used herein, the term "normal cells" refers to the cells which do not exhibit uncontrolled cell growth and the ability to metastasize. The term "normal cells" also include but not limited to "benign cells", "non-cancer cells" and "non-malignant cells".

As used herein, the term "overexpress" or "overexpression" refers to increasing the expression of a protein to a level higher than normal cells or non-cancer cells produce.

As used herein, the term "patient" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like.

The term "pharmaceutically acceptable excipient" refers to pharmacologically inactive substances that are added to a pharmaceutical preparation in addition to the active pharmaceutical ingredient. Pharmaceutically acceptable excipients may take the function of vehicle, diluent, release, disintegration or dissolution modifying agent, absorption enhancer, stabilizer or a manufacturing aid among others.

As used herein, the term "therapeutically effective amount" refers to any amount of a compound which, as compared to a corresponding patient who has not received such amount, results in improved treatment, healing, prevention, or amelioration of a disease, disorder, or side effect, or a decrease in the rate of advancement of a disease or disorder.

As used herein, the term "treat," "treating" or "treatment" refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

What is claimed is:

1. A method of treating cancer in a patient, comprising:
administering a therapeutically effective amount of a compound to the patient to treat the cancer,
wherein the compound is represented by Formula I,

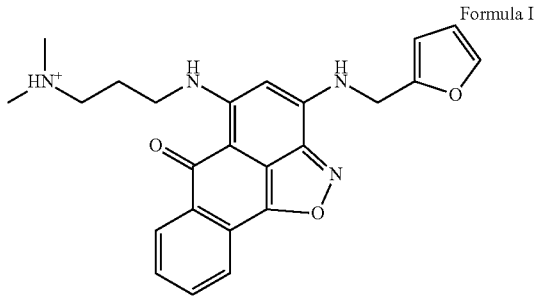 [SMILES: C[NH+](C)CCCNc1cc(NCc2ccco2)c2noc3c2c1C(=O)c1ccccc1-3]

Formula I wherein tumor cells of the cancer express a higher level of Bromodomain Plant Homeodomain Finger Transcription Factor (BPTF) than normal cells express.

2. The method of claim 1, wherein the cancer is selected from a group consisting of colorectal cancer, melanoma, breast cancer, lung adenocarcinoma, and brain cancer.

3. The method of claim 1, wherein the cancer is non-small cell lung cancer.

4. The method of claim 1, wherein the compound is administered in combination with one or more additional BPTF inhibitors.

5. The method of claim 1 further comprising:

obtaining a biological sample from the patient;

detecting whether BPTF is overexpressed in the biological sample by comparing a level of BPTF expression in the biological sample with a level of BPTF expression in a control group; and diagnosing the patient with the cancer when the level of the BPTF expression in the biological sample is higher than that in the control group.

6. The method of claim 5, wherein the biological sample is a tissue sample from the patient.

7. The method of claim 5, wherein the biological sample is a blood sample or a plasma sample from the patient.

8. A method of treating non-small cell lung cancer in a patient, comprising:
administering a therapeutically effective amount of a compound to the patient to treat the non-small cell lung cancer,
wherein the compound is represented by Formula I:

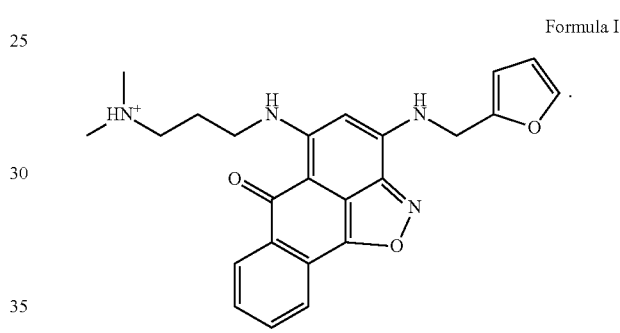

Formula I

9. The method of claim 8, wherein tumor cells of the non-small cell lung cancer express a higher level of Bromodomain Plant Homeodomain Finger Transcription Factor (BPTF) than normal cells express, and wherein the compound is administered in combination with one or more additional BPTF inhibitors to treat the non-small cell lung cancer.

* * * * *